United States Patent [19]

LaPointe et al.

[11] Patent Number: 4,771,518
[45] Date of Patent: Sep. 20, 1988

[54] TAPERED, TUBULAR POLYESTER FABRIC

[75] Inventors: Donat J. E. LaPointe, Fall River, Mass.; Laurence J. Vincent, North Providence, R.I.; Lawrence T. Wright, Whitman, Mass.

[73] Assignee: The United States of America as represented by the Administrator of the National Aeronautics and Space Administration, Washington, D.C.

[21] Appl. No.: 79,320

[22] Filed: Jul. 30, 1987

[51] Int. Cl.⁴ .................. B64D 10/00; B64G 6/00; D03D 3/02; D03D 13/00
[52] U.S. Cl. .................................. 28/143; 2/2.1 A; 2/16; 2/167; 28/165; 138/123; 138/125; 139/387 R; 428/35; 428/229; 428/913
[58] Field of Search ............ 28/165, 143; 139/387 R; 2/2.1 A, 16, 167; 428/35, 229, 913

[56] References Cited

U.S. PATENT DOCUMENTS

| | | | |
|---|---|---|---|
| 1,034,063 | 7/1912 | Bentley | 139/387 R |
| 1,075,249 | 10/1913 | Gaynor | 139/387 R |
| 1,165,775 | 12/1915 | Grossgebauer | 139/387 R |
| 1,186,612 | 6/1916 | Satinover | 139/387 R |
| 2,998,030 | 8/1961 | Koppelman et al. | 139/387 R |
| 3,044,497 | 7/1962 | Rebut | 138/121 |
| 3,094,762 | 6/1963 | Jeckel . | |
| 3,606,656 | 9/1971 | Kumagai et al. . | |
| 3,669,157 | 6/1972 | Woodall, Jr. et al. | 139/387 R |
| 3,719,212 | 3/1973 | Emerson et al. | 139/387 R |
| 4,025,684 | 5/1977 | Neidhardt | 428/257 |
| 4,091,464 | 5/1978 | Vykukal | 2/2.1 A |
| 4,147,822 | 4/1979 | Kallmeyer et al. | 428/35 |

FOREIGN PATENT DOCUMENTS

| | | | |
|---|---|---|---|
| 656594 | 2/1938 | Fed. Rep. of Germany | 139/387 R |
| 15335 | 10/1969 | Netherlands | 139/387 R |

*Primary Examiner*—James C. Cannon
*Attorney, Agent, or Firm*—Edward K. Fein; John R. Manning; Russell E. Schlorff

[57] ABSTRACT

A tapered tubular polyester sleeve as set forth. It has a large end 12 and a small end 14 with a length to be determined. The ratio of taper is also determined by scale factors. All the warp yarns extend to the large end 12. A requisite number of warp yarns 16 extend the full length of the sleeve. Other warp yarns exemplified at 18, 22, 26, 28, 30 and 32 extend from the large end but are terminated along the length of the sleeve. It is then woven with a filling yarn 40 which extends in a full circle along the full length of the sleeve to thereby define the tapered sleeve. The sleeve after fabrication is then placed on a mandrel 42, heated in an oven 44 and is thereafter placed on the arm or other limb of a space suit exemplified at 50.

14 Claims, 1 Drawing Sheet

TAPERED, TUBULAR POLYESTER FABRIC

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The field of invention of this disclosure is a seamless tapered fabric sleeve. It particularly finds use as a form fitted sleeve over the arm of a space suit and the like where the arm is subject to tapering and may also bend, flex or articulate. The arm is protected by the sleeve which is fitted over it and to this end, the surrounding sleeve is ideally constructed so that it contours snugly around the structure. Moreover, the sleeve can be custom sized so that the diameter at one end can be first identified, the diameter of the opposite can be the same or different, and the length of the sleeve between the two ends can be varied. So to speak, the sleeve is a shaped trapezoid when viewed from the side in a flattened state. It is preferably made of a strong material such as polyester and is provided with a controllable degree of skrinkage. In the method of processing, the sleeve is first woven and thereafter placed on a conforming supportive mandrel for skrinkage to reduce the size of the sleeve. In this step, the material shrinks to yield the final sized, tapered sleeve. One mode of shrinkage is by placing the sleeve in an oven at elevated temperature; another mode of shrinkage includes wetting with methylene chloride at room temperature to chemically shrink the sleeve on the mandrel. In this state, it is a seamless, woven element brought down to a particular size and is able to slide over an arm or other mechanism to provide protection to it.

2. Background Art

Representative U.S. Patents thought to have a bearing on the present disclosure include U.S. Pat. No. 4,091,464 which discloses a space suit having joints therein. It appears to incorporate a fiber membrane of aramid fibers with a laminate of neoprene. U.S. Pat. No. 2,998,030 at Columns 1 and 2 is directed to a method of weaving. U.S. Pat. No. 3,094,762 discloses heat shrinking of TFE tubing. U.S. Pat. No. 3,606,656 discloses a woven fabric with heat shrinking of selected fibers while U.S. Pat. No. 3,669,157 shows heat skrinking of a woven tubular fabric. In addition to these, U.S. Pat. No. 3,719,212 shows fabric woven on a mandrel. U.S. Pat. No. 4,025,684 is directed to a woven tubular fabric coated with plastics or synthetic rubbers. Last of all, U.S. Pat. No. 4,147,822 shows a resin impregnated, woven fabric in the composite or layered structure. It would appear that none of the art discussed above teaches the described structure or the method of manufacture thereof.

SUMMARY OF THE INVENTION

The present invention is summarized as both a method of manufacture and a product made thereby. The product is a tapered sleeve which is first formed with a specified diameter at one end, a different diameter at the opposite end and a specified length between the two ends. It is shaped in the fashion of a trapezoid when considered flat but it is a hollow tubular sleeve woven of polyester material and tapers from a large end size to a small size. Moreover, this sleeve is constructed so that, after weaving, it can then be placed on a supportive mandrel and then placed in an oven to be thermally shrunk. An alternative processing step is chemically shrinking the sleeve. Thereafter, the sleeve is placed around the arm of a space suit to serve as a seamless, pressurized tubular structure which spans an articulated space suit arm or leg.

In the method of manufacture, through the use of a standard or conventional textile loom capable of tubular weaving, a set of warp threads is defined extending from one end of the sleeve to be made thereby. Selective warp yarns are cut. The number of yarns cut and the length of yarns before cutting defines the degree or extent of taper. The yarn threads so cut are woven into the tapered sleeve by the filling thereby defining the tapered sleeve. The next step in the process is to place the sleeve on a supportive mandrel for thermal or chemical shrinking the untreated material, thereby reducing diameter and yielding a quality seamless sleeve of tapered construction brought down to a particular set of dimensions for use with a space suit joint system.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
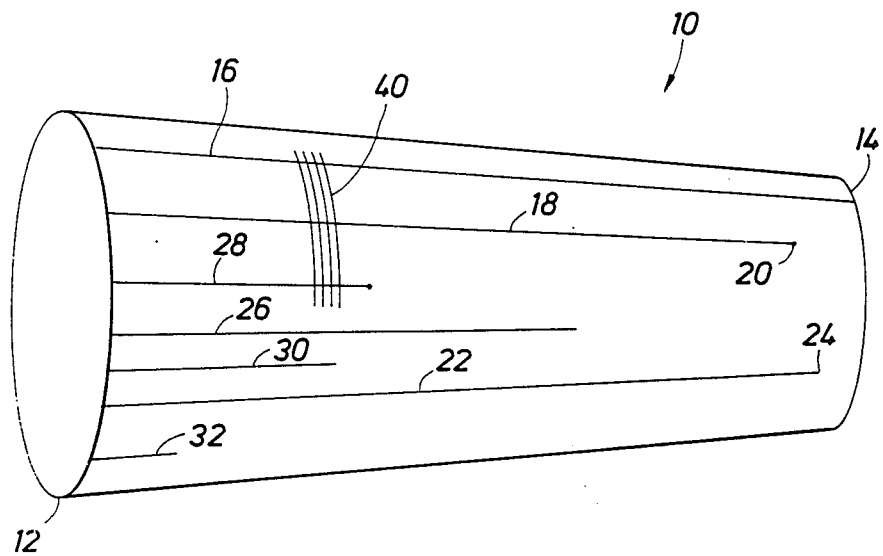
FIG. 1 is a side view of a sleeve during weaving showing deployment of the several yarns which make up the sleeve and illustrating termination of selected warp yarns in the sleeve.

Attention is directed to FIG. 1 of the drawings where the numeral 10 identifies a sleeve which is constructed in accordance with the present disclosure. It is shown at a stage where weaving takes place to assemble the sleeve out of polyester yarn. The sleeve is shown out of the textile loom for ease of description. Textile looms of the sort necessary to weave tubular sleeves are well known. Such a textile loom forms sleeves of requisite dimensions. In this instance, the textile loom is equipped with polyester yarn to obtain the sleeve of the present disclosure.

Considering now the sleeve shown in FIG. 1 of the drawings, it is in the form of a tubular member or sleeve 10 which has a large diameter end 12. The opposite end is identified by the numeral 14 and it is smaller than the end 12. At the time of setting up the textile loom to weave the sleeve 10, several warp yarns are placed in it. One such typical full length warp yarn is identified by the numeral 16. This represents several warp yarns which extend the full length of the sleeve from end to end. Thus, if the sleeve were one meter in length, the warp yarn 16 would be one meter in length. The diameter of the yarn is subject to variation so long as a diameter is selected which can be handled by the textile loom which weaves the sleeve 10. The yarn 16 extends the full length of the sleeve.

Warp yarns are spaced evenly around the sleeve in typical fashion. The ends per inch are thus defined by the required spacing for yarns in the sleeve. This can vary over a range depending on the size of yarn, thickness of the finished fabric, and other scale factors well known. The sleeve 10 is thus formed with several warp yarns 16 extending the full length of the sleeve. In contrast with that particular warp yarn, another warp yarn 18 extends along the sleeve but is terminated at an end location 20. For instance, it can have a length which is 90% of the length of the sleeve 10. The yarn 18 is terminated at the point 20, it being understood that the yarn 18 can be replicated in the sleeve 10. Further, another warp yarn 22 terminates at a point 24. The yarns 18 and 22 are different in length. Proceeding further, yarns 26, 28, 30 and 32 are all shorter yet. Many shorter warp yarns thus define the amount of taper. If the taper is to be severe, then a large number of short yarns is used. That is, along the entire length of sleeve 10, yarns are terminated at spaced locations so that the number of threads is reduced something in a linear fashion along the length of the tubular sleeve to yield the necessary taper. By contrast, if the taper is not severe, the full length yarns 16 are increased while the number of shortened yarns is decreased. In other words, once the dimensions of the tapered sleeve are known, this is implemented by first selecting the relative percentage of yarns which are full length as typified by the yarn 16. For instance, this percentage can be 100% to define a sleeve with no taper or can be 25% to define a sleeve wherein the smaller end is approximately one fourth the size of the larger end of the sleeve. Perhaps an example will aid in this description. Assume a sleeve which has 5,000 yarns at the large end 12. Assume further that the sleeve is to be one meter in length. Assume also that the sleeve is to taper to half the large diameter. In that event, 50% of the yarns in the sleeve will extend the full length as does the yarn 16. In this particular example 2,500 of the yarns will extend the full length of the sleeve. The remaining 2,500 yarns will then terminate evenly along the one meter length of the sleeve. This requires that the 2,500 yarns terminate in the 100 centimeters (the length of the sleeve) or that 25 yarns terminate in each centimeter. In this example, this would then require 2,500 yarns of shortened length evenly distributed along the sleeve 10. In other words, the 2,500 shortened yarns would be evenly distributed along the sleeve length.

An important factor to note is that the shortened yarns are mixed evenly in with the full length yarns 16. To this end, they are mixed and scattered so that they do not collectively terminate at batched locations. This avoids creating an irregularity in the surface of the woven fabric when finished.

In the conventional textile loom which is available for forming such a woven tubular member, the several yarns which make up the warp of the sleeve are thus placed in the textile loom, including both full length yarns and those which are shortened as described above, and the loom is then operated to place the filling yarn 40 through the warp yarns. That is, the filling yarn 40 is woven in a repeated circle from one end of the sleeve to the other. The filling yarn weaving process is believed to be well known for standard textile looms. Suffice it to say that the filling yarn 40 is woven until the full length of the sleeve is defined. In actuality, it might be desirable to weave the sleeve even longer than the desired length to permit trimming of the finished product. Weaving thus forms the sleeve shown in FIG. 1 so that it is a completed product devoid of seams. As desired, the woven sleeve is removed from the textile loom and then has the form shown in FIG. 1. Depending on dimensions and the stiffness of the yarn, the sleeve has a stiffness and weight which is subject to control at the time of selection of dimensions, yarn count and other scale factors relating to the finished product. In summary, the sleeve structure shown in FIG. 1 is woven to provide the defined sleeve.

Figure 2:
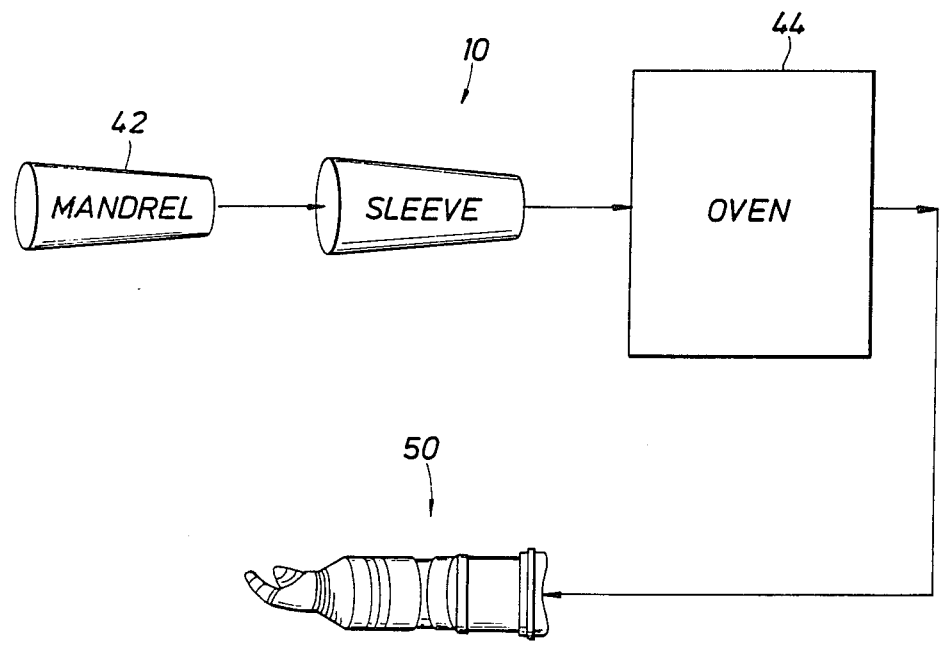
FIG. 2 is a step wise processing sequence showing the sleeve of the present disclosure as it is placed on a mandrel and subsequently treated with a view of making the finished product which is part of a space suit joint system.

The sleeve 10 shown in FIG. 1 is next processed in the manner best illustrated in FIG. 2. The sleeve is supported on a mandrel 42. This holds the sleeve in the desired shape and also keeps the sleeve from folding. The sleeve and mandrel are then placed in an oven 44 and heated to a specified temperature and for a required duration. As stated earlier, the sleeve can also be shrunk chemically by wetting with methylene chloride at ambient temperature causing the fabric to shrink to the contour of the mandrel. After shrinking, the sleeve can thereafter be removed from the mandrel 42. The sleeve then is ready to be placed over a portion of a space suit such as the arm 50 illustrated in FIG. 2. The sleeve then has a proper taper and a length to permit it to be placed over the arm to cover the joint thereof and to provide necessary protection to the space suit arm.

As will be understood from the description given above, several scale factors can be modified and changed in the fabrication of the sleeve. The tapered tubular polyester fabric sleeve is woven to selected scale. While the foregoing is directed to the preferred embodiment, the scope is determined by the claims which follow.

We claim:

1. A method of forming a protective sleeve for a space suit limb comprising the steps of:
   (a) positioning for weaving a set of parallel warp yarns having a length at least equal to that of the sleeve to be made;
   (b) cutting a selected portion of the warp yarns short of the full length of the sleeve wherein all the yarns extend from one end and the number and length of cut yarns determines the extent of taper of the sleeve when finished;
   (c) weaving the sleeve with the filling yarn until the sleeve has been completed; and
   (d) heating the sleeve to shrink the sleeve to a requisite size to thereby obtain a seamless sleeve for subsequent fitting over limbs of a space suit.

2. The method of claim 1 wherein the sleeve is tapered by determining the ratio of the size of the small end to the large end of the sleeve and terminating that portion of yarns in a distributed pattern along the length of the sleeve.

3. The method of claim 2 including the step of weaving the filling of a continuous yarn.

4. The method of claim 3 including the subsequent step of placing the sleeve after weaving on a support mandrel of tapered construction which avoids folding of the sleeve prior to heating for shrinking of the sleeve.

5. The method of claim 4 including the step of placing the sleeve over a limb of a space suit.

6. The method of claim 5 including the step of weaving the sleeve of polyester yarn.

7. A method of forming a protective sleeve for a space suit limb comprising the steps of:
  (a) positioning for weaving a set of parallel warp yarns having a length at least equal to that of the sleeve to be made;
  (b) cutting a selected portion of the warp yarns short of the full length of the sleeve wherein all the yarns extend from one end and the number and length of cut yarns determines the extent of taper of the sleeve when finished;
  (c) weaving the sleeve with the filling yarn until the sleeve has been completed; and
  (d) chemically shrinking the sleeve to a requisite size to thereby obtain a seamless sleeve for subsequent fitting over limbs of a space suit.

8. The method of claim 7 wherein the sleeve is tapered by determining the ratio of the size of the small end to the large end of the sleeve and terminating that portion of yarns in a distributed pattern along the length of the sleeve.

9. The method of claim 8 including the step of weaving the filling of a continuous thread.

10. The method of claim 9 including the subsequent step of placing the sleeve after weaving on a support mandrel of tapered construction which avoids folding of the sleeve prior to shrinking of the sleeve.

11. The method of claim 10 including the step of placing the sleeve over a limb of a space suit.

12. The method of claim 11 including the step of weaving the sleeve of polyester yarn.

13. A tapered shrinkable sleeve comprising an elongate tubular sleeve having a large end and a small end defined by a set of warp yarns all extending from the large end of the sleeve, and wherein selected of the warp yarns around the sleeve are terminated without extending to the small end, said warp yarns being woven with a filling yarn in circular deployment therearound to yield a seamless sleeve.

14. The sleeve of claim 13 wherein the yarns are shrinkable polyester yarn having a yarn density sufficient that, on shrinkage, a solid fabric is formed.

* * * * *

UNITED STATES PATENT AND TRADEMARK OFFICE
CERTIFICATE OF CORRECTION

PATENT NO.   : 4,771,518
DATED        : Sep. 20, 1988
INVENTOR(S)  : Frederic S. Dawn, Joseph J. Kosmo, J. E. LaPointe,
               Laurence J. Vincent, and Lawrence T. Wright It is certified that error appears in the above-identified patent and that said Letters Patent is hereby corrected as shown below:

Title page:

Please correct Item 75, adding the following names:

Frederic S. Dawn, Houston, TX;
    Joseph J. Kosmo, Seabrook, TX

Signed and Sealed this

Eighth Day of August, 1989

*Attest:*

DONALD J. QUIGG

*Attesting Officer*       *Commissioner of Patents and Trademarks*